(12) United States Patent
Hauer et al.

(10) Patent No.: US 10,964,459 B2
(45) Date of Patent: Mar. 30, 2021

(54) ELECTRICAL RESISTOR, IN PARTICULAR FOR MEDICAL IMPLANTS

(71) Applicant: BIOTRONIK SE & CO. KG, Berlin (DE)

(72) Inventors: Marc Hauer, Uster (CH); Birgit Neubauer, Horb (DE); Jochen Held, Arth (CH); Martin Henschel, Berlin (DE); Thomas Pfefferkorn, Berlin (DE); Alexander Dettmer, Berlin (DE)

(73) Assignee: Biotronik SE & Co. KG, Berlin (DE)

( * ) Notice: Subject to any disclaimer, the term of this patent is extended or adjusted under 35 U.S.C. 154(b) by 0 days.

(21) Appl. No.: 16/254,886

(22) Filed: Jan. 23, 2019

(65) Prior Publication Data
US 2019/0228887 A1 Jul. 25, 2019

(30) Foreign Application Priority Data

Jan. 23, 2018 (DE) ...................... 10 2018 101 419.8
Apr. 27, 2018 (EP) .................................. 18169787.1

(51) Int. Cl.
H01C 1/14 (2006.01)
H01C 1/084 (2006.01)
H01C 17/28 (2006.01)
H01C 1/142 (2006.01)
H01C 1/012 (2006.01)
H01C 17/06 (2006.01)
A61N 1/39 (2006.01)

(52) U.S. Cl.
CPC ............... H01C 1/14 (2013.01); H01C 1/012 (2013.01); H01C 1/084 (2013.01); H01C 1/142 (2013.01); H01C 17/06 (2013.01); H01C 17/28 (2013.01); A61N 1/3956 (2013.01)

(58) Field of Classification Search
CPC .......... H01C 1/14; H01C 1/012; H01C 1/084; H01C 1/142; H01C 17/06; H01C 17/28
See application file for complete search history.

(56) References Cited

U.S. PATENT DOCUMENTS 3,835,434 A * 9/1974 Kahn .................. H01C 1/1406
338/22 R
4,297,670 A * 10/1981 Solow ...................... H01C 7/06
216/16
5,312,442 A * 5/1994 O'Phelan ................. A61N 1/08
607/5

(Continued)

FOREIGN PATENT DOCUMENTS

DE 112006002516 T5 8/2008
DE 102013226759 A1 6/2015
EP 0841668 A1 5/1998

Primary Examiner — Kyung S Lee
(74) Attorney, Agent, or Firm — Laurence A. Greenberg; Werner H. Sterner; Ralph E. Locher

(57) ABSTRACT

An electrical resistor has a resistance conductor, which is applied to a carrier layer, and two connection elements, which are electrically conductively connected to the resistance conductor. The two connection elements are configured to each be welded or soldered to an electrical contact in order to electrically contact the resistor. The resistance conductor for each connection element has a region that overlaps the corresponding connection element. The overlap region is in electrical contact with the corresponding connection element.

15 Claims, 3 Drawing Sheets

(56) References Cited

U.S. PATENT DOCUMENTS

| | | | |
|---|---|---|---|
| 6,353,707 B1* | 3/2002 | Loktev | H05B 3/26 |
| | | | 219/213 |
| 7,782,173 B2 | 8/2010 | Urano et al. | |
| 8,183,974 B2* | 5/2012 | Wienand | G01K 1/10 |
| | | | 338/25 |
| 9,265,170 B2 | 2/2016 | Swaminathan et al. | |
| 9,633,768 B2* | 4/2017 | Yoneda | H01C 1/014 |
| 2009/0108986 A1* | 4/2009 | Urano | H01C 1/012 |
| | | | 338/309 |
| 2016/0343479 A1 | 11/2016 | Itou | |
| 2018/0012685 A1* | 1/2018 | Nagase | H01C 1/084 |

* cited by examiner

ELECTRICAL RESISTOR, IN PARTICULAR FOR MEDICAL IMPLANTS

CROSS-REFERENCE TO RELATED APPLICATION

This application claims the priority, under 35 U.S.C. § 119, of European patent application EP 18169787.1, filed Apr. 27, 2018, and of German application No. DE 10 2018 101 419.8, filed Jan. 23, 2018; the prior applications are herewith incorporated by reference in their entirety.

BACKGROUND OF THE INVENTION

Field of the Invention

The invention relates to an electrical resistor, in particular for use as a component in a medical implant.

An implant of this kind can be an implantable defibrillator, for example. A defibrillator of this kind must be able to discharge a charged capacitor within a short period of time so as to return to a controlled starting state. The electrical resistor necessary for this purpose must absorb high energies within a short period of time. Since the resistor is inserted in particular during the final assembly of the defibrillator, it must be possible to join the resistor in an integrally bonded manner, in particular by means of laser welding, so as to satisfy the electrical and mechanical requirements.

Relatively complex process steps are provided in the prior art for this purpose. Here, the resistor is firstly etched from a basic material and is galvanically metallized locally by means of Ni and Au. By means of this metallization a connection band is then connected by way of resistance welding. The weld seam is then insulated with a cover film.

Furthermore, U.S. Pat. No. 9,265,170 B2 discloses an IC with a layered structure, wherein a connection element for the electrical and mechanical connection is mounted subsequently.

SUMMARY OF THE INVENTION

It is an object of the present invention to provide an electrical resistor which can be produced relatively easily and yet still allows the connection elements of the resistor to be joined by means of welding or soldering.

With the above and other objects in view there is provided, in accordance with the invention, an electrical resistor, comprising:
 a carrier layer;
 a resistance conductor applied to the carrier layer; and
 two connection elements each electrically conductively connected to the resistance conductor;
 wherein
 the two connection elements being configured for welding or soldering to an electrical contact; and
 the resistance conductor for each connection element having an overlap region overlapping the respective connection element and electrically conductively connecting the corresponding the connection element.

It is provided here in accordance with the invention that the two connection elements are configured so that they can each be welded or soldered or brazed to an electrical contact in order to electrically contact the resistor, and that the resistance conductor, for each connection element, has a region overlapping the corresponding connection element. The region, which is referred to as an overlap region, electrically conductively connects the corresponding connection element.

In accordance with one embodiment of the resistor of the invention it is provided that each of both connection elements is formed in one piece, e.g. formed or designed as a metal sheet.

The resistance conductor in accordance with one embodiment of the invention can be formed as a coating of the carrier layer. In particular the resistance conductor can be formed by sputter deposition or vapor deposition of an electrically conductive substance or material onto the carrier layer.

In accordance with one embodiment of the resistor according to the invention it is provided that the resistance conductor is arranged on a first side of the carrier layer, wherein a metal layer is arranged on a side of the carrier layer facing away from the first side, which metal layer forms a heat sink for absorbing Joule's heat. The metal layer can be applied directly on the second side of the carrier layer or can be connected thereto in an integrally bonded manner via an adhesive layer. The carrier layer for example can be a film. The carrier layer for example can consist of a plastic, a polymer or a polyimide or can comprise a substance of this kind.

In accordance with one embodiment of the resistor according to the invention it is also provided that the connection elements are arranged on the first side of the carrier layer or are connected thereto in an integrally bonded manner.

In accordance with one embodiment of the resistor according to the invention it is also provided that the connection elements form portions of the metal layer and/or that the connection elements are arranged on the second side of the carrier layer. The connection elements can be connected to the second side of the carrier layer for example via an adhesive layer.

In accordance with one embodiment of the resistor according to the invention it is also provided that the various regions of the resistance conductor each form a plated through-hole, wherein said regions each extend through a through-opening in the carrier layer and electrically conductively connect the corresponding connection element.

It is also provided in accordance with one embodiment of the resistor according to the invention that a metal layer is applied to each of the regions of the resistance conductor for local resistance reduction, such that each region is arranged between the corresponding metal layer and the corresponding connection element. Each metal layer can consist of Cu or can comprise Cu. Each metal layer can be formed by deposition of a conductive material (for example Cu) on the corresponding region.

In accordance with one embodiment of the resistor according to the invention it is also provided that the metal layer or heat sink comprises one of the following substances or consists of one of the following substances: Cu; an alloy comprising Cu and Ni; Ni; Nb; Ta; a high-grade steel; an alloy comprising Cu, Ni and Mn; an alloy comprising 55% by weight Cu, 44% by weight Ni and 1% by weight Mn.

In accordance with one embodiment of the resistor according to the invention it is also provided that the two regions of the resistance conductor are connected to one another via a meandering portion of the resistance conductor (for example in each case integrally or in one piece).

In accordance with one embodiment of the resistor according to the invention it is also provided that the resistance conductor consists of one of the following metals or comprises one of the following metals: Ti, Au, Cu, Ni, Pd, Nb, Cr.

In accordance with one embodiment of the resistor according to the invention it is also provided that the resistor has a first and a second insulation layer, wherein the first insulation layer is connected or adhesively bonded via an adhesive layer to the first side of the carrier layer and at the same time covers the resistance conductor, and wherein the second insulation layer is connected or adhesively bonded via an adhesive layer to the second side of the carrier layer and/or to the heat sink, wherein the second insulation layer covers the heat sink (apart from part of the connection elements). The two insulation layers in particular each form an outermost top layer of the resistor.

It is also provided in accordance with one embodiment of the resistor according to the invention that the connection elements protrude from the resistor between the two insulation layers, such that said connection elements each can be welded or soldered to a further component or a contact.

In accordance with a further aspect the present invention relates to an implantable defibrillator comprising a resistor according to the invention.

In accordance with one embodiment of the implantable defibrillator of the invention it is provided that the resistor is electrically conductively connected to a capacitor.

With the above and other objects in view there is also provided, in accordance with the invention, a method that comprises the following steps:

connecting a carrier layer to a metal layer, wherein the metal layer forms a heat sink of the resistor and two connection elements of the resistor, forming a separate through-opening for each of the connection elements, each of said through-openings being associated with the corresponding connection element and extending through the carrier layer towards the associated connection element, and applying an electrically conductive material to a first side of the carrier layer so as to form a resistance conductor, such that the resistance conductor extends through the corresponding through-opening towards the corresponding connection element and contacts this electrically conductively, whereupon an electrically conductive connection is produced between the resistance conductor and the two connection elements.

In accordance with one embodiment of the method according to the invention it is provided that the electrically conductive material in order to form the resistance conductor is applied to the carrier layer by coating the carrier layer with said material.

It is also provided in accordance with one embodiment of the method according to the invention that the electrically conductive material in order to form the resistance conductor is applied to the carrier layer by sputter deposition of said material.

It is also provided in accordance with one embodiment of the method according to the invention that the electrically conductive material in order to form the resistance conductor is applied to the carrier layer by vapor deposition of said material on the carrier layer.

The electrically conductive material of the resistance conductor can be one of the following substances or the material can comprise one of the following substances: Ti, Au, Cu, Ni, Pd, Nb, Cr (see also above).

In accordance with one embodiment of the method according to the invention it is also provided that the carrier layer comprises one of the following substances or consists of one of the following substances: a plastic, a polymer, a polyimide. The carrier layer can be formed in particular as a film.

It is also provided in accordance with one embodiment of the method according to the invention that the metal layer comprises one of the following substances or consists of one of the following substances (see also above): Cu, an alloy comprising Cu and Ni; Ni; Nb; Ta; a high-grade steel; an alloy comprising Cu, Ni and Mn; an alloy comprising 55% by weight Cu, 44% by weight Ni and 1% by weight Mn (this alloy is also referred to as Constantan).

In accordance with one embodiment of the method according to the invention it is also provided that the metal layer is formed as a sheet which is adhesively bonded to the carrier layer or film.

In accordance with one embodiment of the method it can also be provided that, for resistance reduction, a metal layer is applied to each region of the resistance conductor that in each through-opening extends as far as the corresponding connection element and electrically contacts it. Each metal layer can be formed by deposition of a conductive material (in particular metal, such as Cu) on the region in question.

In accordance with one embodiment of the method according to the invention it is also provided that a first insulation layer is adhesively bonded to the first side of the carrier layer, and therefore the resistance conductor is covered, wherein a second insulation layer is adhesively bonded to a second side of the carrier layer and/or to the metal layer, and therefore the metal layer (apart from a portion of the termination elements) is covered. The second side of the carrier layer in particular faces away from the first side of the carrier layer.

In the invention described above a resistance region or resistance conductor is advantageously connected directly to the welding region or the connection elements. A plurality of resistors can be produced here simultaneously/in parallel. In addition, due to the omission of the mixed connection consisting of basic material and connection band, it is possible to dispense with a costly galvanic Ni/Au deposition and a complex welding process. It is hereby in turn possible to dispense with an additional insulation layer and a corresponding insulation test.

The invention furthermore advantageously allows the use of various substances or metals as resistance conductors (such as Ti, Au, Cu, Ni, Pd, Pt, Nb, etc.). The use of alternative materials which have an increasing electrical resistance with increasing temperature advantageously ensures adaptive current limitation within the resistance conductor during capacitor discharge of a defibrillator. The current limitation in turn has a favorable effect on the further temperature increase and thus on the stability of the resistance conductor and the surrounding materials.

Other features which are considered as characteristic for the invention are set forth in the appended claims.

Although the invention is illustrated and described herein as embodied in an electrical resistor, in particular for medical implants, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following

DETAILED DESCRIPTION OF THE INVENTION

Figure 1:
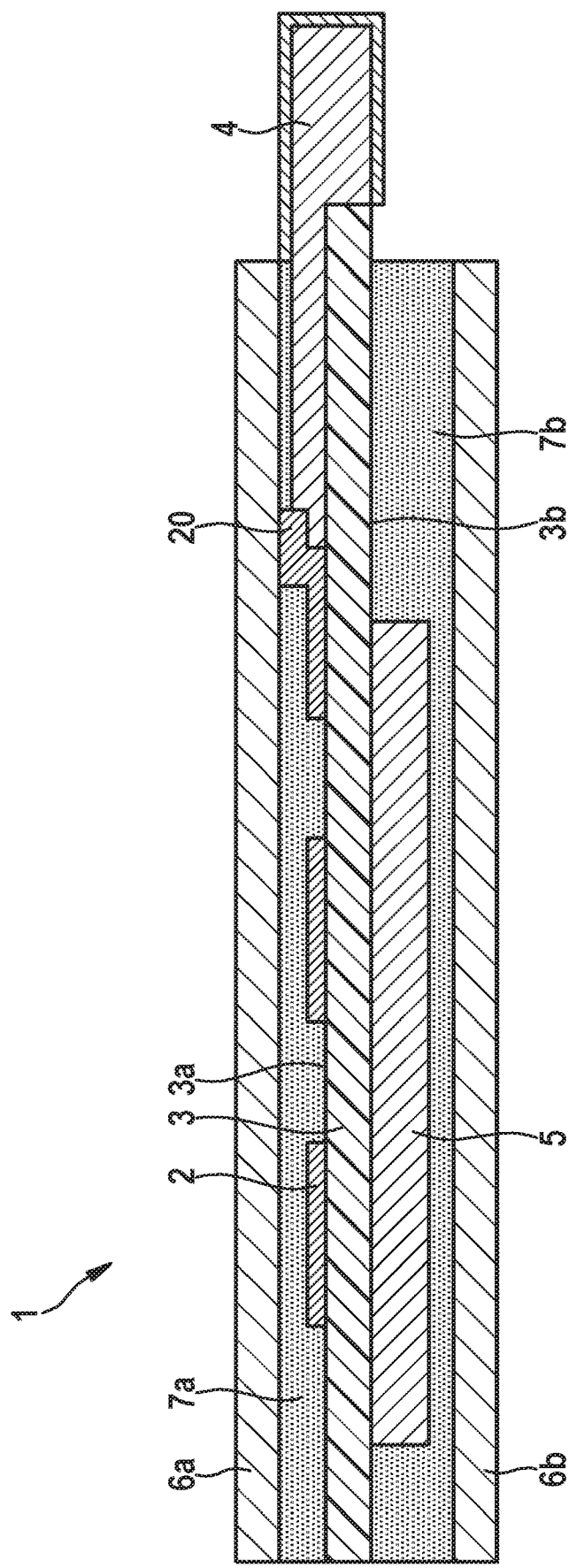
FIG. 1 is a schematic sectional illustration of an embodiment of a resistor according to the invention.

Referring now to the figures of the drawing in detail and first, particularly, to FIG. 1 thereof, there is shown a schematic sectional illustration of an electrical resistor according to the invention. The electrical resistor is particularly suited for use in an implantable defibrillator.

The resistor 1 comprises a resistance conductor 2, which is mounted on a carrier layer 3, and two connection elements 4, which are electrically conductively connected to the resistance conductor 2. It is provided in accordance with the invention that the two connection elements 4 are configured each to be welded (in particular by laser welding) or soldered to an electrical contact in order to electrically contact the resistor 1, and that the resistance conductor 2 has overlap regions 20 that each overlap with a separate one of the connection elements 4. Each of the overlap regions 20 electrically conductively contact the corresponding connection element 4. In FIG. 1 only one connection element 4 is shown on account of the sectional illustration. The second connection element lies in a plane parallel to the drawing plane and is overlapped identically by a region of the resistance conductor 2.

In order to produce the resistance conductor 2, titanium (Ti) can be deposited on the carrier layer 3, for example by means of a thin-film process. The titanium resistance conductor 2 can overlap here with the connection elements 4, which are each formed as a copper structure, and can thus enable a seamless transition. Alternative materials for the resistance conductor 2 are, for example, Au, Cu, Ni, Pd, Pt, Nb, Cr or combinations of these materials.

Each connection element 4 can be exposed in a region, for example by means of a laser, such that said region can be used as a welded contact or connection band. Each element 4 makes it possible to guide a welded contact seamlessly out of a printed circuit board.

A heat sink 5 in the form of a metal layer (for example Cu) is provided on the second side 3b of the carrier layer and is used to absorb heat that is created during an electrical pulse of the defibrillator.

As a last production step, the metal structures 2, 20, 4 and 5 on both sides 3a, 3b of the carrier layer 3 can also be provided with insulation or top layers 6a, 6b for insulation, which layers are each connected in an integrally bonded manner to the carrier layer 3 via a corresponding adhesive layer 7a, 7b. The connection elements 4 protrude here between the cover layers 6a, 6b.

Figure 2:
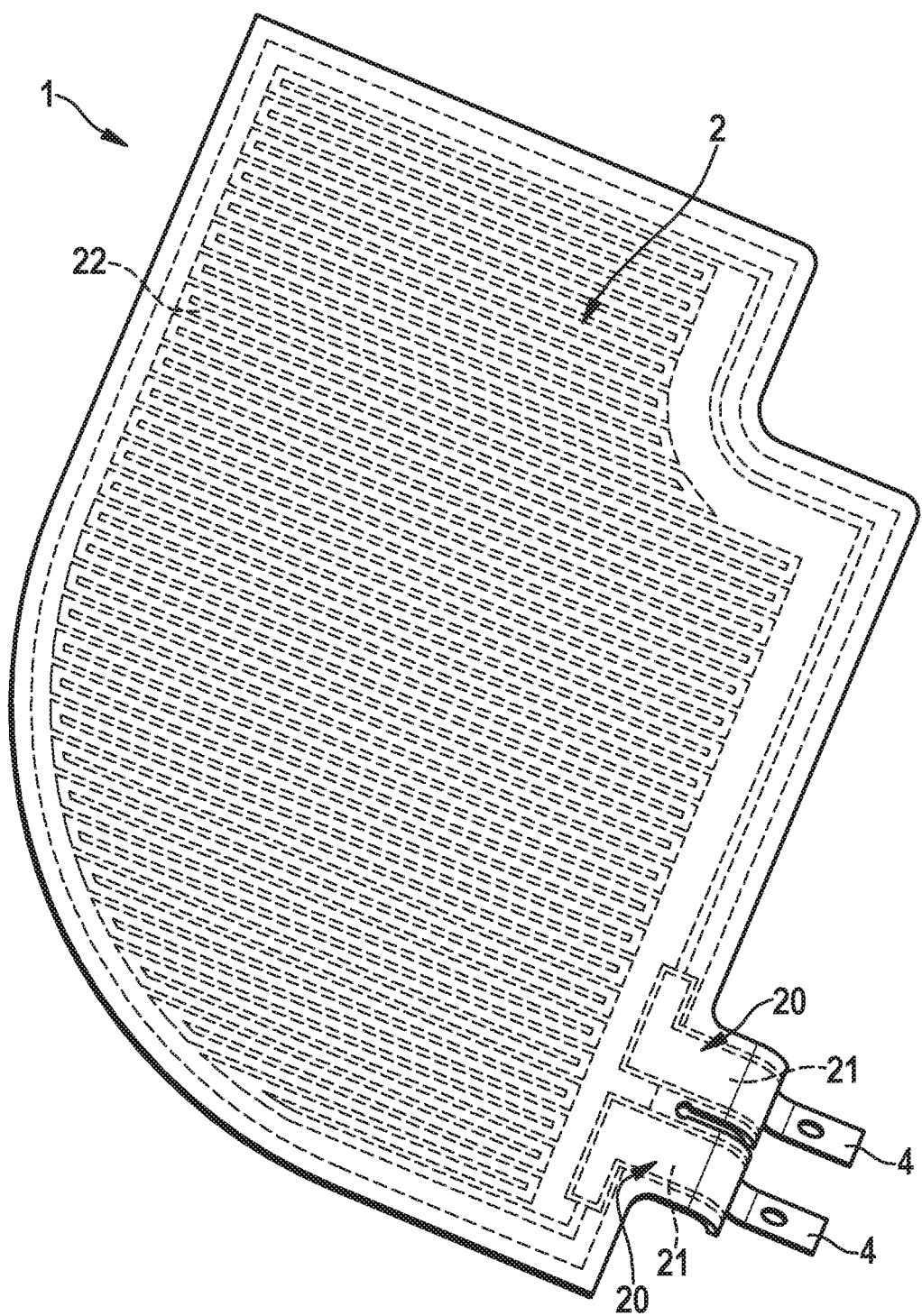
FIG. 2 shows a perspective view of a further embodiment of a resistor according to the invention.
Figure 3:
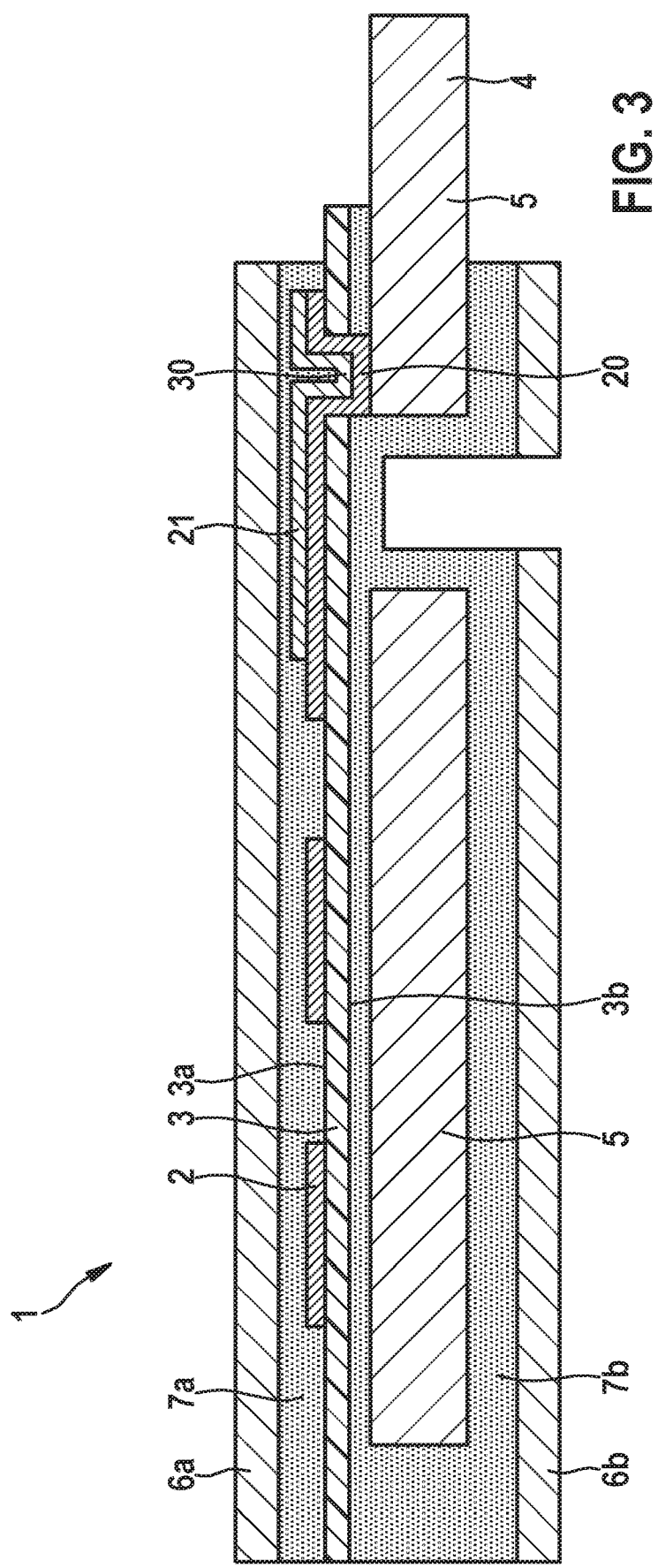
FIG. 3 shows a schematic sectional illustration of the resistor shown in FIG. 2.

FIG. 2 in conjunction with FIG. 3 shows a further embodiment of a resistor 1 according to the invention. In this variant a top film 3 is glued onto a metal layer 5 in the form of a metal sheet 5 made of constantan, which top film forms a carrier layer 3. Alternative materials for the metal layer 5 are for example different CuNi compounds, Ni, Nb, Ta, high-grade steel, etc. The metal layer 5 on the one hand is used here as a heat sink, and on the other hand forms weldable connection elements 4. In order to produce a connection between the resistance conductor 2 and the metal layer 5, a separate through-opening 30 is formed in the carrier layer 3 for each connection element 4 (in FIG. 3 only one through-opening 30 is shown on the basis of the sectional illustration; the other one is disposed in a plane parallel to the drawing plane), for example by means of a laser. If the material of the resistance conductor 2 (for example titanium) is then deposited on the first side 3a of the carrier layer 3 (for example by sputter deposition or by vapor deposition), overlap regions 20 of the resistance conductor 2 that protrude in each case into corresponding through-openings 30 and contact the connection element 4 or the metal layer 5 exposed there (plated through-hole) are created simultaneously.

In accordance with one embodiment of the present description the carrier layer 3 comprises more than one through-opening 30, wherein additional through-openings can be arranged in planes that are parallel to the plane shown in FIG. 3. Additional through-openings can be arranged adjacently to one another, for example beside the through-opening 30 in FIG. 3. In one embodiment of the invention the carrier layer 3 comprises through-openings adjacent to one another. In a preferred embodiment the carrier layer 3 comprises a total of 9 through-openings.

A metal layer 21 (for example made of Cu) can be partially deposited on the titanium of each overlap region 20 of the resistance conductor 2. This reduces the electrical resistance locally and makes it possible for a performance drop to occur only in the region in which the heat can be absorbed by the metal layer 5 or heat sink.

As a last step, the metal structures 2, 20, 21, 4 and 5 can in turn be provided on both sides 3a, 3b of the carrier layer 3 for insulation by means of insulation or cover layers 6a, 6b, which are each connected in an integrally bonded manner to the carrier layer 3 via an adhesive layer 7a, 7b. The connection elements 4 in turn protrude between the top layers 6a, 6b.

In the above-described embodiments the resistance conductor may have a layer thickness in the range of from 250 nm to 750 nm, in particular 500 nm. Furthermore, the carrier layer 3 may in each case have a layer thickness in the range of from 10 μm to 40 μm, in particular 25 μm. The metal layer 5 may in each case have a layer thickness in the range of from 35 μm to 100 μm. Each metal layer 21 may have a layer thickness in the range of from 1 μm to 20 μm. The connection elements 4 may each have a layer thickness in the range of from 35 μm to 100 μm. The insulation layers 6a, 6b for example may have a layer thickness of 25 μm. Lastly, the adhesive layers 7a, 7b may have a layer thickness in the range of from 25 μm to 75 μm.

It will be understood that the aforementioned values for the individual layer thicknesses are but examples of the invention. Values deviating herefrom may also be possible.

The invention claimed is:

1. An electrical resistor, comprising:
    a carrier layer having a first side and a second side facing away from the first side;
    a resistance conductor applied to the first side of said carrier layer; and
    two connection elements each electrically conductively connected to said resistance conductor;
    each of said two connection elements being configured for welding or soldering to a respective electrical contact;

said resistance conductor having an overlap region for each connection element, said overlap region overlapping the respective said connection element and electrically conductively connecting the corresponding said connection element;
a metal layer disposed on the second side of said carrier layer, said metal layer forming a heat sink; and
wherein at least one of the following is true: said connection elements form portions of said metal layer or said connection elements are arranged on the second side of said carrier layer.

2. The electrical resistor according to claim 1, wherein said connection elements are arranged on the first side of the carrier layer.

3. The electrical resistor according to claim 1, wherein said metal layer comprises a material selected from the group consisting of Cu; an alloy comprising Cu and Ni; Ni; Nb; Ta; a high-grade steel; an alloy comprising Cu, Ni and Mn; and an alloy comprising 55% by weight Cu, 44% by weight Ni and 1% by weight Mn.

4. The electrical resistor according to claim 1, wherein said metal layer consists of a material selected from the group consisting of Cu; an alloy comprising Cu and Ni; Ni; Nb; Ta; a high-grade steel; an alloy comprising Cu, Ni and Mn; and an alloy comprising 55% by weight Cu, 44% by weight Ni and 1% by weight Mn.

5. The electrical resistor according to claim 1, wherein said two regions of said resistance conductor are connected to one another via a meandering portion of said resistance conductor.

6. The electrical resistor according to claim 1, wherein said resistance conductor consists of a metal selected from the group consisting of Ti, Au, Cu, Ni, Pd, Nb and Cr.

7. The electrical resistor according to claim 1, wherein said resistance conductor comprises at least one metal selected from the group consisting of Ti, Au, Cu, Ni, Pd, Nb and Cr.

8. An implantable defibrillator comprising an electrical resistor according to claim 1.

9. An electrical resistor, comprising:
a carrier layer;
a resistance conductor applied to said carrier layer; and
two connection elements each electrically conductively connected to said resistance conductor;
each of said two connection elements being configured for welding or soldering to a respective electrical contact; and
said resistance conductor for each connection element having an overlap region overlapping the respective said connection element and electrically conductively connecting the corresponding said connection element, each of said overlap regions forming a plated through-hole, each of said regions extending through a through-opening in said carrier layer and electrically conductively connecting the corresponding said connection element.

10. The electrical resistor according to claim 9, comprising a metal layer applied to each of said overlap regions for local resistance reduction, with each said overlap region being arranged between the corresponding said metal layer and the corresponding said connection element.

11. An electrical resistor, comprising:
a carrier layer;
a resistance conductor applied to said carrier layer; and
two connection elements each electrically conductively connected to said resistance conductor;
each of said two connection elements being configured for welding or soldering to a respective electrical contact; and
said resistance conductor having an overlap region for each connection element, said overlap region overlapping the respective said connection element and electrically conductively connecting the corresponding said connection element, wherein said resistance conductor is arranged on a first side of said carrier layer, and a metal layer is disposed on a second side of said carrier layer facing away from the first side, said metal layer forming a heat sink;
first and second insulation layers, said first insulation layer being connected via an adhesive layer to the first side of said carrier layer and covering said resistance conductor, and said second insulation layer being connected via an adhesive layer to a second side of said carrier layer and/or to said metal layer, wherein said second insulation layer covers said metal layer at least in portions thereof.

12. The electrical resistor according to claim 11, wherein said connection elements protrude from said resistor between said two insulation layers.

13. A method of producing an electrical resistor, the method comprising the following steps:
connecting a carrier layer to a metal layer, the metal layer forming a heat sink of the resistor and two connection elements of the resistor;
forming a separate through-opening for each of the connection elements, each of the through-openings being associated with the corresponding connection element and extending through the carrier layer towards the associated connection element; and
applying an electrically conductive material to a first side of the carrier layer so as to form a resistance conductor, with the resistance conductor extending through the corresponding through-opening towards the corresponding connection element and contacting the respective connection element electrically conductively, and thereby producing an electrically conductive connection between the resistance conductor and the two connection elements.

14. The method according to claim 13, which comprises, in order to form the resistance conductor, applying the electrically conductive material to the carrier layer by coating the carrier layer with the material.

15. The method according to claim 13, which comprises:
adhesively bonding a first insulation layer to the first side of the carrier layer, and thereby covering the resistance conductor;
adhesively bonding a second insulation layer to a second side of the carrier layer averted from the first side and/or to the metal layer to thereby cover the metal layer at least in some portions.

* * * * *